United States Patent [19]

Simmons et al.

[11] 4,017,547

[45] Apr. 12, 1977

[54] OXIDATION OF p-XYLENE TO TEREPHTHALALDEHYDE

[75] Inventors: Kenneth E. Simmons; James E. Williams, both of Kingsport, Tenn.

[73] Assignee: Eastman Kodak Company, Rochester, N.Y.

[22] Filed: Sept. 8, 1975

[21] Appl. No.: 611,381

[52] U.S. Cl. .............................. 260/599; 252/467
[51] Int. Cl.² ........................................ C07C 45/02
[58] Field of Search .................................. 260/599

[56] References Cited

UNITED STATES PATENTS

| | | | |
|---|---|---|---|
| 3,485,876 | 12/1969 | van de Mond | 260/599 |
| 3,597,485 | 8/1971 | Brill | 260/599 |
| 3,845,137 | 10/1974 | Magder | 260/599 |

Primary Examiner—Bernard Helfin
Attorney, Agent, or Firm—J. Frederick Thomsen; Daniel B. Reece, III

[57] ABSTRACT

Terephthalaldehyde is produced by the vapor phase oxidation of p-xylene in the presence of a catalyst mixture of tungsten in the form of an oxide or silicotungstic acid, molybdenum in the form of an oxide and bismuth in the form of an oxide.

7 Claims, No Drawings

OXIDATION OF P-XYLENE TO TEREPHTHALALDEHYDE

This invention concerns an improved process for the vapor phase oxidation of p-xylene to terephthalaldehyde using a catalytic amount of a novel catalyst composition.

U.S. Pat. No. 3,597,485 discloses a process for preparation of terephthalaldehyde (referred to herein as TPAA) which comprises subjecting p-xylene to a vapor phase oxidation in the presence of a catalyst mixture consisting of tungsten and molybdenum.

U.S. Pat. No. 3,845,137 describes a process for preparation of TPAA in which p-xylene is oxidized in the vapor phase in the presence of a supported catalyst mixture of oxides of tungsten and molybdenum and at least one third metal or oxide selected from the group consisting of calcium, barium, titanium, zirconium, hafnium, thallium, niobium, zinc and tin. According to this patent, the three component catalyst composition possesses improved catalyst life when compared to the catalyst described in U.S. Pat. No. 3,597,485. However, in both of these patents the conversion of p-xylene to TPAA is low.

We have discovered that in the vapor phase oxidation of p-xylene in the presence of catalytic amount of a mixture of tungsten in the form of an oxide or silicotungstic acid, and an oxide of molybdenum, the conversion of p-xylene to TPAA is improved substantially by the addition to the catalyst composition of a catalytically effective amount of an oxide of bismuth. Not only is the conversion of p-xylene to TPAA increased substantially by the use of an oxide of bismuth, but catalyst life is improved considerably, thereby permitting the operation of the oxidation process for much longer periods of time before the reactor must be recharged with fresh catalyst. These two primary advantages are of utmost importance for the operation of the oxidation process continuously on a commercial scale.

The catalyst composition used in one improved process is a mixture of tungsten, bismuth and molybdenum in an atom ratio of between about 5:0.5:1 and 20:2:1, the preferred ratio being about 10:1:1. The catalyst mixture preferably is deposited on a suitable catalyst support such as, for example, low surface area alumina, silica or silicon carbide which is the preferred support. The support preferably has a surface area of about 0.01 to 1 m²/g with about 0.1 to 0.5 m²/g being especially preferred. The weight percent of the tungsten, bismuth and molybdenum on the support can be in the range of about 5 to 10. The novel catalyst composition therefore consists essentially of tungsten as an oxide or silicotungstic acid, molybdenum as an oxide and bismuth as an oxide as the essential catalytic ingredients.

The catalysts used in the novel process of our invention are prepared according to known techniques. Typically, aqueous solutions of water-soluble compounds containing tungsten, bismuth and molybdenum are mixed in a manner to give a tungsten to bismuth to molybdenum atom ratio of between about 5:0.5:1 and 20:2:1. A suitable carrier is added to the resulting solution and the solution is evaporated while the support is mixed thoroughly with the solution. The dried catalyst then is calcined, for example, by heating at about 250° C. for about 2 hours and at 500° C. for 2 hours. Examples of the water-soluble compounds which can be used in preparing the catalysts include ammonium paratungstate, ammonium metatungstate, silicotungstic acid, ammonium molybdate, silicomolybdic acid, phosphomolybdic acid and bismuth nitrate.

The reaction temperature used in our improved process should be sufficiently high so that a desirable rate of oxidation occurs, but not so high as to cause undesirable side reactions. Thus, temperatures in the range of 525° to 625° C., preferably 550° to 600° C., may be employed. Atmospheric pressure may be used, but both moderately elevated or reduced pressures may be employed if desired.

The contact times of reactants with the catalyst may be between 0.01 and 1 second with the preferred contact time being about 0.1 to 0.2 second. Although the air to p-xylene mole ratio may be varied widely, for example, between about 100:1 to 200:1, we prefer the ratio is in the range being about 125:1 to 175:1.

Our improved process utilizing the novel catalyst composition described above is further illustrated by the following examples.

Oxidations in the following examples were carried out at a reaction temperature of 550° C. and atmospheric pressure with a contact time of 0.2 second $$\frac{\text{(ml of total feed per second calculated at reaction temperature and pressure)}}{\text{bulk volume of catalyst, ml}}$$

One mole of p-xylene was fed to the reactor for every 172 moles of air fed. The reactor used in these examples was a three-foot long, one-inch diameter Vycor glass tube which was heated by a three-element tubular electric furnace. The reactor was charged with approximately 35 ml of catalyst. Conversions and yields of terephthalaldehyde were based on quantitative gas chromatographic analyses of solutions of the reaction products.

The terms conversion and yield are defined by the following expressions:

$$\% \text{ Conversion to terephthalaldehyde} = \frac{\text{moles of terephthalaldehyde produced} \times 100}{\text{moles of p-xylene fed}}$$

$$\% \text{ Yield of terephthalaldehyde} = \frac{\text{moles of terephthalaldehyde produced} \times 100}{\text{moles of p-xylene consumed}}$$

EXAMPLE 1

A catalyst composition of 0.5% $MoO_3$ + 1% $Bi_2O_3$ + 10% silicotungstic acid on silicon carbide was prepared as follows: ammonium molybdate (0.28 g) and silicotungstic acid (5.26 g of a solution having an assay of 0.72 g $WO_3$ per g) were dissolved in approximately 20 ml of water. Bismuth nitrate [$Bi(NO_3)_3 \cdot 5H_2O$, 0.94 g] was dissolved in approximately 25 ml of dilute nitric acid. These solutions were mixed and combined with 40 g of silicon carbide support (Carborundum Co. type CHO, 8 + 20 mesh granules). Drying was accomplished on a steam bath with manual stirring. Further drying was done in a vacuum oven at 125° C., followed by calcination at 250° C. (2 hr) and 500° C. (2 hours). The catalyst has a W to Bi to Mo atom ratio of 10.3:1.2:1. p-Xylene was oxidized over this catalyst by feeding air at approximately 3.3 l./min STP, and p-xylene at approximately 0.11 ml/min. The product collection apparatus consisted of a 2 in.-diameter, air-cooled U-tube which was 10 in. long, and a Vigreux column 2 ft. long. Downstream, unreacted p-xylene was collected in two traps which were cooled with dry ice in n-butyl alcohol.

The reactor was operated for a period of 6 hr during which a quantity of 34.4 g of p-xylene was fed. The terephthalaldehyde which was collected in the U-tube and Vigreux column was dissolved in acetone and the solution diluted to 500 ml. Analysis of the solution indicated that it contained 17.7 g of terephthalaldehyde and 1.5 g of p-tolualdehyde by-product. Material collected in the dry ice traps was diluted to 250 ml with isobutyl acetate. Analysis of the solution indicated that it contained 8.0 g of p-xylene and 1.25 g of p-tolualdehyde. Hence, the conversion of p-xylene to terephthalaldehyde was 41% and the yield was 54%.

EXAMPLE 2

The catalyst preparation of Example 1 was repeated. This 0.5% $MoO_3$ + 1% $Bi_2O_3$ + 10% silicotungstic acid on silicon carbide catalyst was used to oxidize p-xylene in the same manner as Example 1. The reactor was operated for a period of 6 hr during which a quantity of 34.4 g of p-xylene was fed. The terephthalaldehyde which was collected in the U-tube and Vigreux column was dissolved in acetone and the solution diluted to 500 ml. Analysis of the solution indicated that it contained 19.7 g of terephthalaldehyde and 0.75 g of p-tolualdehyde by-product. Material collected in the dry ice traps was diluted to 250 ml with isobutyl acetate. Analysis of the solution indicated that it contained 4.6 of p-xylene and 1.04 g of p-tolualdehyde. The conversion of p-xylene to terephthalaldehyde was 45%, with a yield of 52%.

EXAMPLE 3

A catalyst composition of 0.5% $MoO_3$ + 1% $Bi_2O_3$ + 8.4% $WO_3$ on silicon carbide was prepared as follows: ammonium molybdate (0.27 g) and ammonium metatungstate (4.43 g) were dissolved in approximately 20 ml of water. Bismuth nitrate (0.92 g) was dissolved in approximately 25 ml of dilute nitric acid. These solutions were mixed and combined with 40 g of silicon carbide support. Drying and calcination were accomplished as in Example 1. This catalyst, having a W to Bi to Mo ratio of 10.3:1.2:1, was used to oxidize p-xylene as described in Example 1. The reactor was operated for a period of 6 hr during which a quantity of 34.4 g of p-xylene was fed. The terephthalaldehyde which was collected in the U-tube and Vigreux column was dissolved in acetone and the solution diluted to 500 ml. Analysis of the solution indicated that it contained 20.6 g of terephthalaldehyde and 0.45 g of p-tolualdehyde by-product. Material collected in the dry ice traps was diluted to 250 ml with isobutyl acetate. Analysis of the solution indicated that it contained 2.7 g of p-xylene and 1.13 g of p-tolualdehyde. The conversion of p-xylene to terephthalaldehyde was 47%, with a yield of 52%.

EXAMPLE 4

A 0.6% $MoO_3$ + 9.7% $WO_3$ on silicon carbide catalyst was prepared by dissolving 0.95 g ammonium molybdate and 13.5 g ammonium metatungstate in water and combining these solutions with 100 g of silicon carbide catalyst support. Drying and calcination were accomplished as in Example 1. p-Xylene was oxidized over this catalyst in the same manner as Example 1. The reactor was operated for a period of 6 hr during which a quantity of 34.4 g of p-xylene was fed. The terephthalaldehyde which was collected in the U-tube and Vigreux column was dissolved in acetone and the solution diluted to 500 ml. Analysis of the solution indicated that it contained 12.75 g of terephthalaldehyde and 0.5 g of p-tolualdehyde by-product. Material collected in the dry ice traps was diluted to 250 ml with isobutyl acetate. Analysis of the solution indicated that it contained 14.4 g of p-xylene and 1.0 g of p-tolualdehyde. The conversion of p-xylene to terephthalaldehyde was 29%, with a yield of 50%.

EXAMPLE 5

A catalyst composition of 0.3% $MoO_3$ + 1% $Bi_2O_3$ + 6% $WO_3$ on silicon carbide was prepared as follows: ammonium molybdate (0.20 g) and ammonium metatungstate (3.84 g) were dissolved in approximately 20 ml of water. Bismuth nitrate (1.12 g) was dissolved in approximately 25 ml of dilute nitric acid. These solutions were mixed and combined with 50 g of silicon carbide support. The catalyst was dried and calcined as in Example 1 and was used to oxidize p-xylene as described in Example 1. The catalyst had a W to Bi to Mo atom ratio of 12:2:1. The reactor was operated for a period of 6 hr during which a quantity of 34.4 g of p-xylene was fed. The terephthalaldehyde which was collected in the U-tube and Vigreux column was dissolved in acetone and the solution diluted to 500 ml. Analysis of the solution indicated that it contained 19.1 g of terephthalaldehyde and 0.61 g of p-tolualdehyde by-product. Material collected in the dry ice traps was diluted to 250 ml with isobutyl acetate. Analysis of the solution indicated that it contained 6.1 g of p-xylene and 1.25 g of p-tolualdehyde. The conversion of p-xylene to terephthalaldehyde was 44%, with a yield of 54%.

EXAMPLE 6

The catalyst preparation of Example 1 was repeated. This 0.5% $MoO_3$ + 1% $Bi_2O_3$ + 10% silicotungstic acid on silicon carbide catalyst was used to oxidize p-xylene in a 1 foot long, 1 inch diameter reactor. The catalyst charge was approximately 10 ml and a 1-liter flask was substituted for the U-tube collector. Air was fed at a rate of approximately 943 ml/min STP, and p-xylene was fed at a rate of approximately 0.03 ml/min. The reactor was operated for a period of 6 hr. during which a quantity of 9.7 g of p-xylene was fed. The terephthalaldehyde which was collected in the flask and Vigreux column was dissolved in acetone and the solution diluted to 250 ml. Analysis of the solution indicated that it contained 5.13 g of terephthalaldehyde and 0.25 g of p-tolualdehyde by-product. Material collected in the dry ice traps was diluted to 100 ml with isobutyl acetate. Analysis of the solution indicated that it contained 1.39 g of p-xylene and 0.25 g of p-tolualdehyde. The conversion of p-xylene to terephthalaldehyde was 42%, with a yield of 49%.

EXAMPLE 7

A 1% Bi$_2$O$_3$ + 10% silicotungstic acid on silicon carbide catalyst was prepared by dissolving 2.25 g silicotungstic acid in approximately 10 ml of water and 0.47 g of bismuth nitrate in approximately 15 ml of dilute nitric acid. The solutions were mixed and combined with 20 g of silicon carbide support. Drying and calcination were done as described in Example 1, and p-xylene was oxidized over this catalyst in the same manner as Example 6. The reactor was operated for a period of 6 hr during which a quantity of 9.7 g of p-xylene was fed. The terephthalaldehyde which was collected in the flask and Vigreux column was dissolved in acetone and the solution diluted to 250 ml. Analysis of the solution indicated that it contained 1.25 g of terephthalaldehyde. No p-tolualdehyde by-product was detected. Material collected in the dry ice traps was diluted to 100 ml with isobutyl acetate. Analysis of the solution indicated that it contained 5.90 g of p-xylene and 0.2 g of p-tolualdehyde. The conversion of p-xylene to terephthalaldehyde was 10%, with a yield of 26%.

EXAMPLE 8

A catalyst composition of 0.5% MoO$_3$ + 1% Bi$_2$O$_3$ on silicon carbide was prepared as follows: ammonium molybdate (0.12 g) was dissolved in approximately 10 ml of water and bismuth nitrate (0.42 g) in approximately 15 ml of dilute nitric acid. The solutions were mixed and combined with 20 g of silicon carbide support. After drying and calcination as described in Example 1, oxidation of p-xylene was attempted over this material in the manner of Example 6. Very little reaction occurred (1% conversion, 3% yield).

EXAMPLE 9

The catalyst preparation of Example 1 was repeated. This 0.5% MoO$_3$ + 1% Bi$_2$O$_3$ + 10% silicotungstic acid on silicon carbide catalyst was used in the oxidation of p-xylene as described in Example 1. The reactor was operated continuously over two five-day periods. Samples were collected and analyzed every 12 hr. As indicated in Table 1, initial conversion to terephthalaldehyde was 39%, with a yield of 53%. Conversion was steady for 2.5 days, then declined slowly to 27% after 10 days. Yield increased steadily from 53 to 63%.

Table I

| Total Time Hr. | p-Xylene Fed. g. | p-Xylene Recovered g. | TPAA Produced g. | Conversion to TPAA, % | Yield of TPAA, % |
|---|---|---|---|---|---|
| 12 | 69.0 | 18.75 | 33.9 | 39 | 53 |
| 24 | 68.1 | 19.75 | 34.1 | 40 | 56 |
| 36 | 68.6 | 20.6 | 33.9 | 39 | 56 |
| 48 | 67.7 | 22.1 | 34.2 | 40 | 59 |
| 60 | 68.8 | 22.75 | 34.5 | 40 | 59 |
| 72 | 68.4 | 24.9 | 31.7 | 37 | 58 |
| 84 | 68.7 | 26.8 | 32.0 | 37 | 60 |
| 96 | 68.1 | 27.2 | 30.5 | 34 | 59 |
| 108 | 68.7 | 30.0 | 30.3 | 35 | 62 |
| 116 | 45.2 | 19.3 | 18.6 | 33 | 57 |
| Run interrupted; Air fed at 550° C. over weekend. | | | | | |
| 140 | 68.9 | 31.9 | 29.5 | 34 | 63 |
| 164 | 68.9 | 35.2 | 26.3 | 30 | 62 |
| 188 | 68.7 | 33.4 | 25.9 | 30 | 58 |
| 212 | 68.6 | 36.6 | 25.2 | 29 | 62 |
| 234 | 56.8 | 32.6 | 19.4 | 27 | 63 |

EXAMPLE 10

The catalyst preparation of Example 3 was repeated. This catalyst, composed of 0.5% MoO$_3$ + 1% Bi$_2$O$_3$ + 8.4% WO$_3$ on silicon carbide, was used in the oxidation of p-xylene as described in Example 6. The reactor was operated continuously over two five-day periods. Samples were collected and analyzed every 12 hr. Table II shows that the conversion to terephthalaldehyde initially was 42%, but declined steadily to 25% after 10 days. Yield increased from 49 to 56%.

Table II

| Total Time Hr. | p-Xylene Fed. g. | p-Xylene Recovered g. | TPAA Produced g. | Conversion to TPAA, % | Yield of TPAA, % |
|---|---|---|---|---|---|
| 12 | 19.35 | 2.75 | 10.20 | 42 | 49 |
| 24 | 19.78 | 5.25 | 9.25 | 37 | 50 |
| 36 | 19.61 | 6.19 | 8.92 | 36 | 52 |
| 48 | 19.50 | 7.03 | 9.00 | 36 | 57 |
| 60 | 19.52 | 7.04 | 8.65 | 35 | 55 |
| 72 | 19.35 | 7.80 | 7.83 | 32 | 54 |
| 84 | 19.09 | 7.92 | 7.74 | 32 | 55 |
| 96 | 20.01 | 8.15 | 7.65 | 30 | 51 |
| 108 | 19.01 | 8.54 | 7.43 | 31 | 56 |
| 116 | 13.0 | 6.38 | 4.75 | 29 | 57 |
| Run interrupted; Air fed at 550° C. over weekend. | | | | | |
| 140 | 19.69 | 9.74 | 7.00 | 28 | 56 |
| 164 | 19.61 | 10.40 | 6.38 | 26 | 55 |
| 188 | 19.61 | 9.95 | 6.40 | 26 | 53 |
| 212 | 19.44 | 10.29 | 6.23 | 25 | 54 |
| 234 | 16.34 | 9.00 | 5.15 | 25 | 56 |

EXAMPLE 11

A 0.6% MoO$_3$ + 9.7% WO$_3$ + 0.2% ZrO$_2$ on silicon carbide catalyst was prepared by dissolving 0.45 g ammonium molybdate, 6.7 g ammonium metatungstate, and 0.95 g zirconium acetate solution (13% ZrO$_2$) in ca. 45 ml of water and combining the solution with 50 g of silicon carbide support. Drying and calcination of the catalyst, and use of the catalyst for p-xylene oxidation were done in the same manner as Example 1. The reactor was operated continuously for 240 hours. Samples were collected and analyzed every 12 hours. Initial conversion to terephthalaldehyde was 28%, with a yield of 39%. Conversion declined steadily to 16% and yield was 44% after 240 hours.

EXAMPLE 12

A catalyst composition of 0.64% MoO$_3$ + 9.95% WO$_3$ + 0.055% ZrO$_2$ on silicon carbide was prepared as follows: ammonium molybdate (0.88 g), ammonium metatungstate (13.22 g), and zirconium nitrate [Zr(NO$_3$)$_2$·2H$_2$O, 0.13 g] were dissolved in ca. 90 ml of water and combined with 100 g of silicon carbide support. The catalyst was dried and calcined as described in Example 1. The reactor was operated continuously for 203 hours. Samples were collected and analyzed every 12 hours. Initial conversion to terephthaldehyde was 32%, with a yield of 53%. Conversion declined steadily to 16% and yield declined slightly to 40% after 203 hours.

Although the invention has been described in considerable detail with particular reference to certain preferred embodiments thereof, variations and modifications can be effected within the spirit and scope of the invention.

We claim:

1. In a process for preparing terephthalaldehyde by the vapor phase oxidation of p-xylene in the presence of a supported catalyst mixture of molybdenum in the form of an oxide and tungsten in the form of an oxide or silicotungstic acid, the improvement which comprises employing an oxide of bismuth on the supported catalyst.

2. The process of claim 1 wherein the bismuth to molybdenum atom ratio is about 0.5:1 to 2:1.

3. The process of claim 1 wherein the tungsten to bismuth to molybdenum atom ratio is about 5:0.5:1 to 20:2:1.

4. A process for the preparation of terephthalaldehyde which comprises contacting a mixture of p-xylene and an oxygen-containing gas with a supported catalyst mixture of tungsten in the form of an oxide or silicotungstic acid, molybdenum in the form of an oxide and bismuth in the form of an oxide at a temperature of about 525° to 625° C.

5. The process of claim 4 in which the mixture is contacted with the catalyst for about 0.01 to 1 second and the tungsten to bismuth to molybdenum atom ratio is about 5:0.5:1 to 20:2:1.

6. A process for the preparation of terephthalaldehyde which comprises contacting for about 0.1 to 0.2 second a mixture of p-xylene and air in a p-xylene to air mole ratio of about 1:100 to 1:200 with a supported catalyst mixture of tungsten in the form of an oxide or silicotungstic acid, molybdenum in the form of an oxide and bismuth in the form of an oxide at a temperature of about 550° to 600° C., wherein the tungsten to bismuth to molybdenum atom ratio is about 10:1:1 and the support has a surface area of about 0.01 to 1.0 square meters per gram.

7. The process of claim 6 wherein the contact time is about 0.2 second, the p-xylene to air mole ratio is about 1:172, the temperature is about 550° C. and the support has a surface area of about 0.1 to 0.5 square meters per gram.

* * * * *